United States Patent
Iwai et al.

(10) Patent No.: US 7,326,800 B2
(45) Date of Patent: Feb. 5, 2008

(54) NITROGEN-CONTAINING ORGANOSILICON COMPOUND, METHOD OF MANUFACTURE, AND METHOD OF TREATING SURFACES

(75) Inventors: Makoto Iwai, Ichihara (JP); Mitsuyoshi Hamada, Abiko (JP)

(73) Assignee: Dow Corning Toray Company, Ltd., Chiyoda-Ku Tokyo (JP)

( * ) Notice: Subject to any disclaimer, the term of this patent is extended or adjusted under 35 U.S.C. 154(b) by 0 days.

(21) Appl. No.: 10/551,528

(22) PCT Filed: Mar. 30, 2004

(86) PCT No.: PCT/JP2004/004562

§ 371 (c)(1), (2), (4) Date: Aug. 24, 2006

(87) PCT Pub. No.: WO2004/087719

PCT Pub. Date: Oct. 14, 2004

(65) Prior Publication Data

US 2006/0287546 A1     Dec. 21, 2006

(30) Foreign Application Priority Data

Mar. 31, 2003   (JP)  ............................ 2003-093337

(51) Int. Cl. *C07F 7/04* (2006.01)

(52) U.S. Cl. ...................................... 556/418; 556/482
(58) Field of Classification Search ..................... None
See application file for complete search history.

(56) References Cited

U.S. PATENT DOCUMENTS

| 3,033,815 A | 5/1962 | Pike et al. |
| 4,026,880 A | 5/1977 | Mitchell |
| 4,209,455 A | 6/1980 | Pepe |
| 5,476,884 A | 12/1995 | Kayaba et al. |

FOREIGN PATENT DOCUMENTS

| GB | 882051 | 11/1961 |
| GB | 1394206 | 5/1975 |
| JP | 2002193976 | 9/2005 |

OTHER PUBLICATIONS

English language Abstract for JP 2002-193976 extracted from espacenet.com database dated Aug. 8, 2006.

*Primary Examiner*—Samuel A. Barts
(74) *Attorney, Agent, or Firm*—Howard & Howard Attorneys, P.C.

(57) ABSTRACT

A new nitrogen-containing organosilicon compound contains tertiary amine groups and carbonyl groups wherein the tertiary amine groups are selected from R1R2N— (where R1 and R2 are the same or different univalent hydrocarbon groups of 1-15 carbon atoms), alicyclic amino groups, or heterocyclic amino groups containing in their rings one or more tertiary amine groups.

4 Claims, 1 Drawing Sheet

NITROGEN-CONTAINING ORGANOSILICON COMPOUND, METHOD OF MANUFACTURE, AND METHOD OF TREATING SURFACES

RELATED APPLICATIONS

This application claims priority to and all the advantages of International Application No. PCT/US2004/004562, filed on Mar. 30, 2004, which claims priority to Japanese Patent Application No. 2003-093337, filed on Mar. 25, 2003.

FIELD OF THE INVENTION

This invention is related to a nitrogen-containing organosilicon compound and to a method of manufacture, as well as to a silane coupling agent prepared from the nitrogen-containing organosilicon compound.

BACKGROUND OF THE INVENTION

Organosilicon compounds that contain amino groups and alkoxysilyl groups are used as silane coupling agents. For example, alkoxysilanes that contain primary amino groups and expressed by the formulae

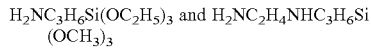

are known.

However, a disadvantage of such compounds is that when compounds that contain primary amino groups are used in conjunction with organic resins, such as epoxy resins that utilize amines as curing catalysts, the amino-group containing compounds exert an adverse effect on the curability of the resins. Therefore, it has been proposed to use alkoxysilanes of the formulae shown as disclosed in U.S. Pat. No. 5,476,884 and JP 2002-193976 A, with secondary amino groups such as $PhNHC_3H_6Si(OCH_3)_3$ where Ph is a phenyl group, $CH_3(CH_2)_3NHC_3H_6Si(OCH_3)_3$, or alkoxysilanes with tertiary amino groups such as $(C_4H_9)_2NC_3H_6Si(OCH_3)_3$.

Although the alkoxysilanes with such secondary or tertiary amino groups reduce the effect on curability of the resins to some extent, their adhesion-improving effect with respect to various substrates is insignificant, and their silane coupling function is insufficient. Another disadvantage of the last mentioned compounds is that, in the manufacturing process, they produce a large amount of by-products in the form of amine hydrochloric salts.

On the other hand, organosilicon compounds with amide groups are known in the art including alkoxysilanes such as $H_2NCONHC_3H_6Si(OC_2H_5)_3$ and $H_2NCOC_3H_6Si(OC_2H_5)_3$ as in U.S. Pat. No. 3,033,815 (May 8, 1962). Furthermore, U.S. Pat. No. 4,209,455 (Jun. 24, 1980) discloses alkoxysilanes which contain secondary amide groups such as $H_2NC_2H_4NHCOC_3H_6Si(OC_2H_5)_3$ and $C_{18}H_{37}NHCOC_2H_4NHC_3H_6Si(OC_2H_5)_3$.

However, even these alkoxysilanes still exert unfavorable effect on curability and adhesion-imparting properties of the resins, and therefore are not yet sufficient in their function as silane coupling agents.

SUMMARY OF THE INVENTION

It is therefore an object of the present invention to provide novel nitrogen-containing organosilicon compounds with tertiary amino and carbonyl groups.

It is another object to provide a method for manufacturing such nitrogen-containing compounds, and silane coupling agents prepared from these nitrogen-containing organosilicon compounds.

These and other features of the invention will become apparent from a consideration of the detailed description.

DETAILED DESCRIPTION OF THE INVENTION

Figure 1:
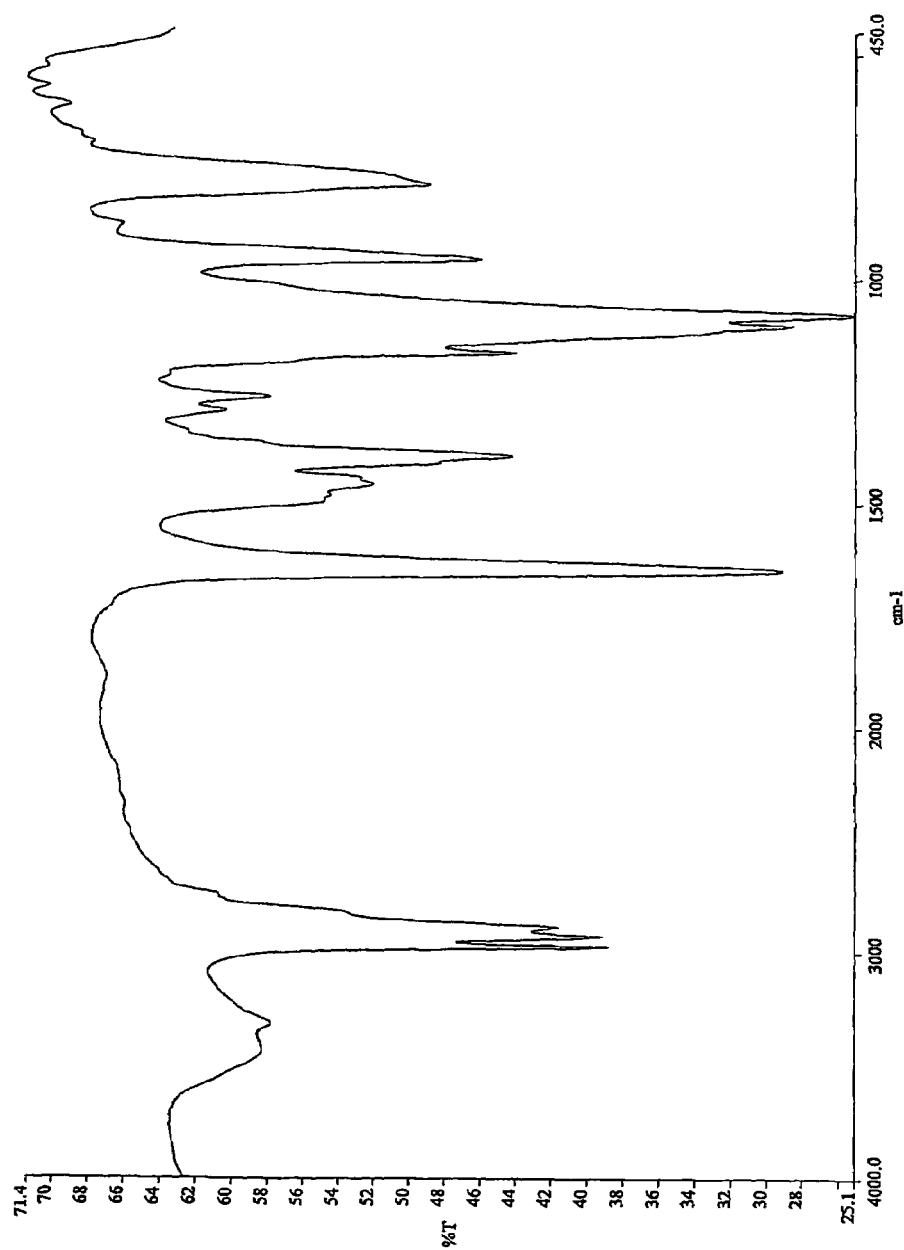
FIG. 1 is a graph that shows an IR spectrum of the nitrogen-containing organosilicon compound obtained in Practical Example 1.

The present invention relates to nitrogen-containing organosilicon compounds of the following general Formula(I) and to a method for manufacturing the compounds:

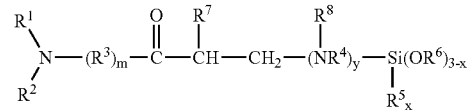

where $R^1$ and $R^2$ are the same or different univalent hydrocarbon groups with 1-15 carbon atoms, $R^3$ is a bivalent hydrocarbon group with 1-15 carbon atoms, or an alkyleneoxy group of the formula $-C_nH_{2n}O-$ where n is an integer from 1-15; $R^4$ is a bivalent hydrocarbon group with 1-15 carbon atoms; $R^5$ is a univalent hydrocarbon group with 1-15 carbon atoms; $R^6$ is a univalent hydrocarbon group with 1-15 carbon atoms or an alkoxyalkyl group; $R^7$ is an alkyl group such as methyl or a hydrogen atom; $R^8$ is a hydrogen atom, an alkyl group with 1-20 carbon atoms, or an aryl group; m is 0 or 1; x is 0-2; and y is 1-5.

The invention also relates to nitrogen-containing organosilicon compounds of general Formula (II) below and to a method for manufacturing such compounds

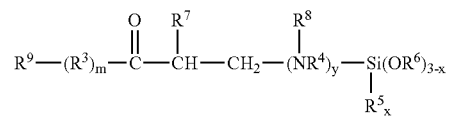

where $R^9$ is an alicyclic amino group or a heterocyclic amino group composed of 1-4 nitrogen atoms, 3-17 carbon atoms, 0-2 oxygen atoms, and 4-34 hydrogen atoms; $R^3$ is a bivalent hydrocarbon group with 1-15 carbon atoms or an alkyleneoxy group of the formula $-C_nH_{2n}O-$ where n is 1-15; $R^4$ is a bivalent hydrocarbon group with 1-15 carbon atoms; $R^5$ is a univalent hydrocarbon group with 1-15 carbon atoms; $R^6$ is a univalent hydrocarbon group with 1-15 carbon atoms or an alkoxyalkyl group; $R^7$ is a an alkyl group such as methyl or a hydrogen atom; $R^8$ is a hydrogen atom, an alkyl group with 1-20 carbon atoms, or an aryl group; m is 0 or 1; x is 0-2; and y is 1-5.

The invention also relates to silane coupling agents prepared from nitrogen-containing organosilicon compounds represented by general Formulae (I) or (II) above.

In general, the nitrogen-containing organosilicon compounds of the present invention are silane compounds represented by general Formulae (I) and (II). In those Formulae, $R^1$ and $R^2$ may designate the same or different univalent hydrocarbon groups with 1-15 carbon atoms including alkyl groups such as methyl groups, ethyl groups, propyl groups, and butyl groups; alkenyl groups such as vinyl groups, allyl groups, and butenyl groups; aryl groups such as phenyl groups, tolyl groups, and xylyl groups; and aralkyl groups such as benzyl groups and phenethyl groups.

Of these groups, most preferred because of availability are alkyl groups, especially methyl or ethyl groups. In the above formulae: $R^3$ is a bivalent hydrocarbon group with 1-15 carbon atoms or an alkyleneoxy group of the formula —$C_nH_{2n}O$— where n is 1-15, as well as a bivalent hydrocarbon group including alkylene groups such as methylene groups, ethylene groups, propylene groups, pentylene groups, and hexylene groups; arylene groups such as phenylene groups, naphthalenyl groups, and biphenylene groups; phenyl substituted alkylene groups such as 4,4'-bismethylene phenyl groups, 3,4'-bismethylenephenyl groups, and 4,4'-bis-ethylenephenyl groups; alkylene arylene groups such as 4,4'-bis-methylenebiphenylene groups; and alkyleneoxy groups such as —$CH_2O$—, —$C_2H_4O$—, and —$C_3H_6O$—. Of these groups, most preferred for ease of synthesis are alkylene groups and alkyleneoxy groups.

In the above formulae, $R^4$ indicates bivalent hydrocarbon groups with 1-15 carbon atoms including alkylene groups such as methylene groups, ethylene groups, propylene groups, pentylene groups, and hexylene groups; arylene groups such as phenylene groups, naphthalenyl groups, and biphenylene groups; phenyl substituted groups such as 4,4'-bismethylene phenyl groups, 3,4'-bismethylene phenyl groups, and 4,4'-bisethylene phenyl groups; and alkylene arylene groups such as 4,4'-bismethylene biphenylene groups. Of these, most preferred as being readily available are alkylene groups, in particular propylene groups.

In the above formulae, $R^5$ designates univalent hydrocarbon groups with 1-15 carbon atoms including alkyl groups such as methyl groups, ethyl groups, propyl groups, and butyl groups; alkenyl groups such as vinyl groups, allyl groups, and butenyl groups; aryl groups such as phenyl groups, tolyl groups, and xylyl groups; and aralkyl groups such as benzyl groups and phenethyl groups.

$R^6$ designates univalent hydrocarbon groups with 1-15 carbon atoms or alkoxyalkyl groups including alkyl groups such as methyl groups, ethyl groups, propyl groups, and butyl groups; alkenyl groups such as vinyl groups, allyl groups, and butenyl groups; aryl groups such as phenyl groups, tolyl groups, and xylyl groups; aralkyl groups such as benzyl groups, and phenethyl groups; and alkoxyalkyl groups such as methoxyethyl groups, and methoxypropyl groups.

When the nitrogen-containing organosilicon compounds of the present invention are used as silane coupling agents, better reactivity of the compounds can be achieved when $R^5$ and $R^6$ are methyl and ethyl groups.

In the above formulae, $R^7$ designates alkyl groups such as methyl groups or hydrogen atoms; $R^8$ designates a hydrogen atom, an alkyl groups with 1-20 carbon atoms such as methyl groups, ethyl groups, propyl groups, and butyl groups, or aryl groups with 6-20 carbon atoms such as phenyl groups, tolyl groups, and xylyl groups. In each molecule, the $R^8$ groups can be the same or different. Of these, most preferred because of availability are hydrogen atoms. $R^9$ is an alicyclic amino group or a heterocyclic amino group with 1-4 nitrogen atoms, 3-17 carbon atoms, 0-2 oxygen atoms, and 4-34 hydrogen atoms.

Cyclic structures of these groups contain one or more tertiary amino groups. Such groups are exemplified by N-cyclopentylamino groups, N-cyclohexylamino groups, N-cycloheptylamino groups, N-(4-methylcyclohexyl)amino groups, and morpholino groups. Of these, most preferred for availability are N-cyclohexylamino groups or morpholino groups.

In the above formulae, m is 0 or 1; and x is 0-2. Most preferred because of availability and reactivity of coupling agents are groups wherein m and x are equal to 0. In the formulae, y is 1-5, preferably 1 or 2. The following are examples of groups where y is 2: N-ethylene-3-aminopropylene groups, N-ethylene-N'-ethylene-3-aminopropylene groups, N-ethylene-4-aminophenylene groups, and N-ethylene-2-aminoethyl-1-ethylenephenylene groups. Of these, N-ethylene-3-aminopropylene groups are preferred.

The nitrogen-containing organosilicon compounds of the present invention include alkoxysilane compounds such as represented by the following formulae wherein Me represents the methyl group and Et represents the ethyl group:

$(CH_3)_2NCOC_2H_4NHC_3H_6Si(OC_2H_5)_3$ $(CH_3)_2NCOC_2H_4NHC_2H_4NHC_3H_6Si(OCH_3)_3$ $(C_2H_5)_2NCOC_2H_4NHC_3H_6Si(OC_2H_5)_3$ $(C_2H_5)_2NCOC_2H_4NHC_2H_4NHC_3H_6Si(OC_2H_5)_3$ $(n\text{-}C_4H_9)_2NCOC_2H_4NHC_3H_6Si(OC_2H_5)_3$ $(n\text{-}C_4H_9)_2NCOC_2H_4NHC_2H_4NHC_3H_6Si(OCH_3)_3$ $(CH_3)_2NC_2H_4COC_2H_4NHC_3H_6Si(OC_2H_5)_3$ $(CH_3)_2NC_2H_4COC_2H_4NHC_2H_4NHC_3H_6Si(OCH_3)_3$ $(CH_3)_2NC_2H_4OCOC_2H_4NHC_3H_6Si(OCH_3)_3$ $(C_2H_5)_2NC_2H_4OCOC_2H_4NHC_3H_6Si(OC_2H_5)_3$ $(n\text{-}C_4H_9)_2NC_2H_4OCOC_2H_4NHC_3H_6Si(OC_2H_5)_3$ $(CH_3)_2NC_2H_4OCOC_2H_4NHC_2H_4NHC_3H_6Si(OCH_3)_3$

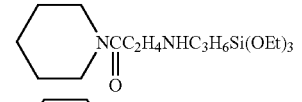

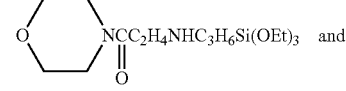 and

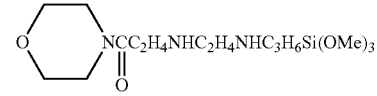

The nitrogen-containing organosilicon compounds of the present invention can be obtained by causing an addition reaction between compound (A) of the following general formula(IV):

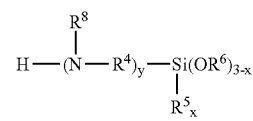

wherein $R^4$, $R^5$, $R^6$, $R^8$, x, and y, are the same as defined above; and a compound (B) of the following general formula (III):

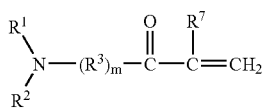

wherein $R^1$, $R^2$, $R^3$, $R^7$, and m, are the same as defined above; or a compound (B) of the following general formula (V):

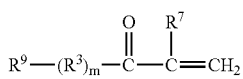

wherein $R^9$, $R^3$, $R^7$, and m, are the same as defined above.

Component (A) represented by the general formula (IV) is a commercially available organosilicon compound such as 3-aminopropyltrimethoxysilane, 3-aminopropyltriethoxysilane, 3-aminoproplmethyldimethoxysilane, 3-aminopropyltri(methoxyethoxy)silane, 4-aminobutyltrimethoxysilane, 5-aminopentyltrimethoxysilane, N-(2-aminoethyl)-3-aminopropyltrimethoxysilane, N-(2-aminoethyl)-3-aminopropyltriethoxysilane, N-(2-aminoethyl)-3-aminopropyltri(methoxyethoxy)silane, and N-(2-aminoethyl)-4-aminobutyltrimethoxysilane. Of these, the most preferred are 3-aminopropyltrimethoxysilane and 3-aminopropyltriethoxysilane.

Component (B) of Formulae (III) or (V) can be a acrylamide or acrylester with tertiary amino groups. These compounds are commercially available and are exemplified by N,N-dimethylacrylamide, N,N-dimethylmethacrylamide, N,N-diethylacrylamide, N,N-dipropylacrylamide, N,N-methylethylacrylamide, N,N-dimethylmethacrylamide, N,N-dibutylmethacrylamide, N-piperazinoacrylamide, N-acryloylmorpholine, N,N-dimethylaminoethylacrylamide, N,N-diethylaminopropylmethacrylamide, 2-(dimethylamino)ethyl acrylate, 2-(diethylamino)ethyl acrylate, and 2-(dibutylamino)ethyl acrylate. Of these, most preferred are N,N-dimethylacrylamide and N-acryloylmorpholine.

Although a reaction of addition between components A and B can be carried out at room temperature, it is preferred to conduct the reaction with heating at a temperature not exceeding 150° C., most preferably at a temperature between 60-100° C. It is also preferred to fill the interior of the reactor with an inert gas such as argon or nitrogen. The addition reaction can be carried out as a consecutive reaction or a one-stage reaction. It is preferred to heat one of the components (A) or (B), while the other component is added gradually.

One distinguishing feature of the invention is that when the nitrogen-containing organosilicon compound is used in conjunction with an organic resin to which an amine functions as a curing catalyst, the unfavorable effect of the compound on curability of the resin is reduced because of the tertiary amine group on the molecular terminal. Another distinguishing feature of the invention is that the nitrogen-containing organosilicon compounds can be produced with high yield using commercially available starting materials. A further distinguishing feature of the manufacturing method of the invention is that the reaction can proceed efficiently even without the use of any catalyst and any solvent. The manufacturing process can be carried out without the use of any special reactor and can be performed on conventional equipment.

The nitrogen-containing organosilicon compounds of the invention provide improved adhesion between various substrates, in particular between organic resins and inorganic materials, or metal materials, when x in the general Formulae (I) and (II) is 0 or 1. Because of these features, nitrogen-containing organosilicon compounds of the present invention are suitable for use as surface-treatment agents, adhesion improvers, primers, and silane coupling agents, for improving the properties of organic resins. The organic resins suitable for purposes of the invention include epoxy resins, phenol resins, urethane resins, melamine resins, polycarbonate resins, polyethylene resins, polyvinylchloride resins, and polyamide resins.

In use as silane coupling agents, the nitrogen-containing organosilicon compounds of general Formulae (I) or (II) may be diluted with water or an organic solvent. The organic solvent suitable for this purpose include methanol, ethanol, or similar water soluble organic solvent. The coupling agent can be applied onto the surface of substrate to be treated or it can be added to the organic resins. The former method is preferred.

Several processes can be used for applying the coupling agent. The coupling agent alone can be sprayed onto the substrate; the coupling agent can be diluted in an organic solvent and the solution can be sprayed onto the surface of the substrate; the coupling agent can be diluted in a water/organic solvent mixture and sprayed onto the substrate; the substrate can be impregnated with the treatment solution obtained with the coupling agent and an organic solvent; and the substrate can be impregnated with the treatment liquid obtained by mixing the coupling agent with the water/organic solvent mixture. These treatments can be completed by the application of heat.

Substrates which can be treated with the silane coupling agent of the invention include powdered materials such as fumed silica, wet-process silica, baked silica, fumed titanium dioxide, powdered quartz, diatomaceous earth, aluminum hydroxide, aluminum oxide, magnesium oxide, aluminosilicate, iron oxide, zinc oxide, calcium oxide, zinc carbonate, mica, and magnesium carbonate; fibrous materials such as glass fiber, Nylon fiber, and carbon fiber; and plates such as glass plates, copper plates, iron plates, stainless-steel plates, and aluminum plates.

EXAMPLES

The following examples are set forth in order to illustrate the invention in more detail.

Practical Example 1

A four neck flask equipped with a thermometer, stirrer, and cooler, was filled with 156.7 parts by weight of 3-aminopropyltriethoxysilane, and the content of the flask was heated in a nitrogenous atmosphere to 70° C. Then, 77.2 parts by weight of N,N-dimethylacrylamide was added dropwise over 30 minutes, and the mixture was stirred and heated for 8 hours at 100° C. The reaction mixture was distilled under a reduced pressure at 138° C. and 1.3 hPa to produce 170.2 parts by weight of a colorless transparent liquid, at a yield of 75 percent. Results of $^{13}C$ nuclear magnetic resonance spectral analysis (NMR), infrared analysis (IR), and GC/MS analysis, defined the product as a nitrogen-containing organosilicon compound of the formula

Practical Example 2

A four neck flask equipped with a thermometer, stirrer, and cooler, was filled with 298.1 parts by weight of 3-aminopropyltrimethoxysilane, and the content of the flask was heated in a nitrogenous atmosphere to 70° C. Then, 181.0 parts by weight of N,N-dimethylacrylamide was added dropwise over 60 minutes, and the mixture was stirred and heated for 8 hours at 100° C. The reaction mixture was distilled under a reduced pressure at 130° C. and 1.3 hPa to produce 360.5 parts by weight of a colorless transparent liquid, at a yield of 78 percent. Results of $^{13}C$ nuclear magnetic resonance spectral analysis (NMR), infrared analysis (IR), and GC/MS analysis, defined the product as a nitrogen-containing organosilicon compound of the formula $(CH_3)_2NCOC_2H_4NHC_3H_6Si(OCH_3)_3$.

Practical Example 3

A four neck flask equipped with a thermometer, stirrer, and cooler, was filled with 33.21 parts by weight of 3-aminopropyltriethoxysilane, and the content of the flask was heated in a nitrogenous atmosphere to 70° C. Then, 23.3 parts by weight of N-acryloyl morpholine was added dropwise over 10 minutes, and the mixture was stirred and heated for 3 hours at 100° C. The reaction mixture was distilled under a reduced pressure at 130° C. and 1.3 hPa to produce 53.7 parts by weight of a yellow transparent liquid, at a yield of 95 percent. Results of $^{13}C$ nuclear magnetic resonance spectral analysis (NMR), and infrared analysis (IR), defined the product as a nitrogen-containing organosilicon compound of the formula

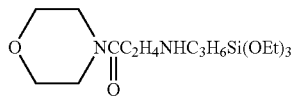

where Et represents the ethyl group.

Practical Example 4

A four neck flask equipped with a thermometer, stirrer, and cooler, was filled with 33.21 parts by weight of 3-aminopropyltriethoxysilane, and the content of the flask was heated in a nitrogenous atmosphere to 70° C. Then, 23.6 parts by weight of 2-(dimethylamino)ethylacrylate was added dropwise over 10 minutes, and the mixture was stirred and heated for 3 hours at 100° C. The reaction mixture was distilled under a reduced pressure at 130° C. and 1.3 hPa to produce 53.7 parts by weight of a yellow transparent liquid, at a yield of 96 percent. Results of $^{13}C$ nuclear magnetic resonance spectral analysis (NMR), and infrared analysis (IR), defined the product as a nitrogen-containing organosilicon compound of the formula $(CH_3)_2NC_2H_4OCOC_2H_4NHC_3H_6Si(OC_2H_5)_3$.

Practical Example 5

A four neck flask equipped with a thermometer, stirrer, and cooler, was filled with 222.4 parts by weight of N-(2-aminoethyl)-3-aminopropyltrimethoxysilane, and the content of the flask was heated in a nitrogenous atmosphere to 70° C. Then, 109.0 parts by weight of N,N-dimethylacrylamide was added dropwise over 30 minutes, and the mixture was stirred and heated for 8 hours at 100° C. The reaction mixture was distilled under a reduced pressure at 130° C. and 1.3 hPa to produce 324.8 parts by weight of a yellowish transparent liquid, at a yield of 98 percent. Results of $^{13}C$ nuclear magnetic resonance spectral analysis (NMR), and infrared analysis (IR), defined the product as a nitrogen-containing organosilicon compound of the formula $(CH_3)_2NCOC_2H_4NHC_2H_4NHC_3H_6Si(OCH_3)_3$.

Practical Example 6

The nitrogen-containing organosilicon compounds obtained in Practical Examples 1-5 were diluted with a mixture of water and ethanol in a 1:1 weight ratio of water to ethanol. This produced treatment liquids with a concentration of 0.4 weight percent of the organosilicon compound. Glass plates were immersed for 10 seconds in these solutions, respectively, and then dried for one hour at 120° C. Then, a curable epoxy resin composition consisting of 100 parts by weight of a bisphenol type A epoxy resin sold under the name EPICOAT 828 having an epoxy equivalent of 185; 8 parts by weight of dicyandiamide; and 0.4 parts by weight of N-dimethylbenzylamine, was applied to the surfaces of the glass plates. The coatings were dried for 90 minutes at 170° C. There was obtained cured epoxy resin coatings firmly adhered to the glass surface, having a cylindrical shape with a 5 mm diameter and 5 mm height.

The coated samples were analyzed for adhesion of the cured epoxy resin using a durometer. The adhesive force was also measured prior and after a Pressure Cooker Test (PCT) which consisted of heating the samples for 24 hours at 121° C. and 100% Relative Humidity. The results of the PCT tests are shown in Table 1.

In Comparative Examples, adhesive force was measured using silane coupling agents as noted below:

Comparative Example 1: $H_2NCONHC_3H_6Si(OC_2H_5)_3$
Comparative Example 2: $PhNHC_3H_6Si(OCH_3)_3$ where Ph is phenyl.
Comparative Example 3: $C_{18}H_{37}NHCOC_2H_4NHC_3H_6Si(OC_2H_5)_3$ The results are shown in Table 1.

TABLE 1

| Example | Adhesive Force (kgf/cm²) | |
| --- | --- | --- |
|  | Prior to PCT | After PCT |
| Practical Example 1 | 140 | 167 |
| Practical Example 2 | 157 | 160 |
| Practical Example 3 | 132 | 128 |
| Practical Example 4 | 140 | 139 |
| Practical Example 5 | 155 | 163 |
| Comparative Example 1 (*) | 118 | 73 |
| Comparative Example 2 (**) | 130 | 79 |
| Comparative Example 3 (***) | 115 | 85 |

In Table 1, (*) is the compound $H_2NCONHC_3H_6Si(OC_2H_5)_3$;
(**) is the compound $PhNHC_3H_6Si(OCH_3)_3$; and
(***) is the compound $C_{18}H_{37}NHCOC_2H_4NHC_3H_6Si(OC_2H_5)_3$.

INDUSTRIAL APPLICABILITY

In view of the above, it should be apparent that the nitrogen-containing organosilicon compounds of the present invention are new and novel compounds containing tertiary-amine and carbonyl groups; that the method for preparing the nitrogen-containing compound provides a high yield; and that when the compounds are used as silane coupling agents, there is obtained improved adhesion between various substrates.

Other variations may be made in compounds, compositions, and methods described herein without departing from the essential features of the invention. The embodiments of the invention specifically illustrated herein are exemplary only and not intended as limitations on their scope except as defined in the appended claims.

The invention claimed is:

1. A nitrogen-containing organosilicon compound of the formula:

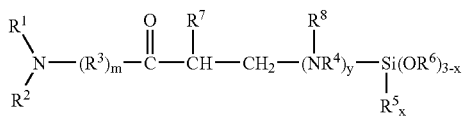

wherein $R^1$ and $R^2$ are the same or different univalent hydrocarbon groups with 1-15 carbon atoms; $R^3$ is a bivalent hydrocarbon group with 1-15 carbon atoms, or an alkyleneoxy group of the formula —$C_nH_{2n}O$— where n is 1-15; $R^4$ is a bivalent hydrocarbon group with 1-15 carbon atoms; $R^5$ is a univalent hydrocarbon group with 1-15 carbon atoms; $R^6$ is a univalent hydrocarbon group with 1-15 carbon atoms or an alkoxyalkyl group; $R^7$ is an alkyl group or a hydrogen atom; $R^8$ is a hydrogen atom, an alkyl group with 1-20 carbon atoms, or an aryl group; m is 0 or 1; x is 0-2; and y is 1-5.

2. A method of manufacturing a nitrogen-containing organosilicon compound defined in claim 1, said method comprising the addition reaction of a compound of the formula;

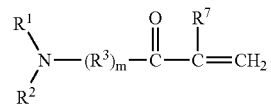

and a compound of the formula:

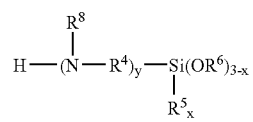

wherein $R^1$ and $R^2$ are the same or different univalent hydrocarbon groups with 1-15 carbon atoms; $R^3$ is a bivalent hydrocarbon group with 1-15 carbon atoms, or an alkyleneoxy group of the formula —$C_nH_{2n}O$— where n is 1-15; $R^4$ is a bivalent hydrocarbon group with 1-15 carbon atoms; $R^5$ is a univalent hydrocarbon group with 1-15 carbon atoms; $R^6$ is a univalent hydrocarbon group with 1-15 carbon atoms or an alkoxyalkyl group; $R^7$ is an alkyl group or a hydrogen atom; $R^8$ is a hydrogen atom, an alkyl group with 1-20 carbon atoms, or an aryl group; m is 0 or 1; x is 0-2; and y is 1-5.

3. A method of treating a surface comprising applying to the surface a nitrogen-containing organosilicon compound according to claim 1.

4. A method of treating a surface comprising applying to the surface a solution containing the nitrogen-containing organosilicon compound according to claim 1.

* * * * *

UNITED STATES PATENT AND TRADEMARK OFFICE
CERTIFICATE OF CORRECTION

PATENT NO. : 7,326,800 B2  Page 1 of 1
APPLICATION NO. : 10/551528
DATED : February 5, 2008
INVENTOR(S) : Makoto Iwai et al.

It is certified that error appears in the above-identified patent and that said Letters Patent is hereby corrected as shown below:

Title Page Item (75) Inventors: after "Iwai", delete "Ichihara" and insert therein --Chiba--

Title Page Item (75) Inventors: after "Hamada", delete "Abiko" and insert therein --Chiba--

Signed and Sealed this

Second Day of September, 2008

JON W. DUDAS
*Director of the United States Patent and Trademark Office*